US008886331B2

(12) United States Patent
Labadie et al.

(10) Patent No.: US 8,886,331 B2
(45) Date of Patent: *Nov. 11, 2014

(54) APPARATUS AND METHODS FOR PERCUTANEOUS COCHLEAR IMPLANTATION

(75) Inventors: Robert F. Labadie, Nashville, TN (US); J. Michael Fitzpatrick, Nashville, TN (US); Jason E. Mitchell, Greenbrier, TN (US); Gregoire S. Blachon, Nashville, TN (US); Jenna Toennies, Nashville, TN (US); Robert J. Webster, III, Nashville, TN (US); Thomas J. Withrow, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/167,964

(22) Filed: Jun. 24, 2011

(65) Prior Publication Data

US 2011/0319913 A1 Dec. 29, 2011

Related U.S. Application Data

(60) Provisional application No. 61/358,579, filed on Jun. 25, 2010.

(51) Int. Cl.
*A61N 1/05* (2006.01)
*A61B 19/00* (2006.01)
*A61B 17/34* (2006.01)

(52) U.S. Cl.
CPC ..... *A61B 17/3403* (2013.01); *A61B 2017/3407* (2013.01); *A61B 19/201* (2013.01); *A61B 19/2203* (2013.01); *A61B 17/3468* (2013.01); *A61B 2019/2226* (2013.01); *A61N 1/0541* (2013.01)

USPC ........................................................... 607/57

(58) Field of Classification Search
None
See application file for complete search history.

(56) References Cited

U.S. PATENT DOCUMENTS 6,273,896 B1   8/2001   Franck et al.
6,529,765 B1   3/2003   Franck et al.
(Continued)

OTHER PUBLICATIONS

Dasgupta B, et.al. The Stewart Platform Manipulator: A Review. Mechanism and Machine Theory 35 (2000) 15-40.*

(Continued)

*Primary Examiner* — Brian T Gedeon
*Assistant Examiner* — Ankit Tejani
(74) *Attorney, Agent, or Firm* — Tim Tingkang Xia, Esq.; Morris, Manning & Martin, LLP

(57) ABSTRACT

A method and apparatus of percutaneous cochlear implantation (PCI). In one embodiment, the method includes the steps of (a) implanting a plurality of anchor members in a skull of a patient surrounding an ear of the patient, (b) attaching a docking frame to the plurality of anchor members, wherein the docking frame has a docking platform and a plurality of fiducial members, (c) acquiring a computed-tomography (CT) image of an area of the patient's head including the ear and the plurality of fiducial members, (d) determining a centroid of each of the plurality of fiducial members and a trajectory for a PCI according to the CT image, (e) configuring a parallel robot by a computer processor according to the CT image such that a top platform of the parallel robot is aligned with the trajectory with respect to the centroids of the plurality of fiducial members, (f) attaching the configured parallel robot to the docking frame, and (g) performing the PCI using one or more surgical tools received by the top platform of the parallel robot.

22 Claims, 12 Drawing Sheets

(56) References Cited

U.S. PATENT DOCUMENTS

| | | | |
|---|---|---|---|
| 2005/0085715 A1* | 4/2005 | Dukesherer et al. | 600/424 |
| 2005/0228266 A1* | 10/2005 | McCombs | 600/414 |
| 2007/0208352 A1* | 9/2007 | Henderson et al. | 606/130 |
| 2009/0157157 A1* | 6/2009 | Schorn et al. | 607/149 |

OTHER PUBLICATIONS

C. Plaskos, P. Cinquin, S. Lavallee, and A. Hodgson, "Praxiteles: a miniature bone-mounted robot for minimal access total knee arthroplasty," Int. J. Med. Robot. Comput. Assist. Surg, vol. 1, No. 4, pp. 67-79, 2005.

S. Song, A. Mor, and B. Jaramaz, "HyBAR: hybrid bone-attached robot for joint arthroplasty," The International Journal of Medical Robotics and Computer Assisted Surgery, vol. 5, No. 2, 2009.

A. Wolf, B. Jaramaz, B. Lisien, and A. DiGioia, "MBARS: mini boneattached robotic system for joint arthroplasty," Int. J. Med. Robot. Comp. Assist. Surg, vol. 1, No. 2, pp. 101-121, 2005.

W. Sukovich, S. Brink-Danan, and M. Hardenbrook, "Miniature robotic guidance for pedicle screw placement in posterior spinal fusion: early clinical experience with the SpineAssistR ," The International Journal of Medical Robotics and Computer Assisted Surgery, vol. 2, No. 2, pp. 114-122, 2006.

L. Joskowicz, R. Shamir, M. Freiman, M. Shoham, E. Zehavi, F. Umansky, and Y. Shoshan, "Image-guided system with miniature robot for precise positioning and targeting in keyhole neurosurgery," Computer Aided Surgery, vol. 11, No. 4, pp. 181-193, 2006.

J. Merlet, Parallel robots. Springer-Verlag New York Inc, 2006.

R. Labadie, R. Balachandran, J. Mitchell, J. Noble, O. Majdani, D. Haynes, M. Bennett, B. Dawant, and J. Fitzpatrick, "Clinical Validation Study of Percutaneous Cochlear Access Using Patient-Customized Microstereotactic Frames," Otology & Neurotology, vol. 31, No. 1, p. 94, 2010.

R. Balachandran, J. Mitchell, G. Blachon, J. Noble, B. Dawant, J. Fitzpatrick, and R. Labadie, "Percutaneous cochlear implant drilling via customized frames: An in vitro study," Otolaryngology-Head and Neck Surgery, vol. 142, No. 3, pp. 421-426, 2010.

J. Noble, F. Warren, R. Labadie, B. Dawant, and J. Fitzpatrick, "Determination of drill paths for percutaneous cochlear access accounting for target positioning error," in Proc. SPIE, vol. 6509, Mar. 2007, p. 650925.1650925.10.

R. Labadie, J. Noble, B. Dawant, R. Balachandran, O. Majdani, and J. Fitzpatrick, "Clinical validation of percutaneous cochlear implant surgery: initial report," Laryngoscope, vol. 118, No. 6, pp. 1031-1039, 2008.

R. Labadie, J. Mitchell, R. Balachandran, and J. Fitzpatrick, "Customized, rapid-production microstereotactic table for surgical targeting: description of concept and in vitro validation," International Journal of Computer Assisted Radiology and Surgery, vol. 4, No. 3, pp. 273-280, 2009.

D. Henderson, "Simple Ceramic Motor . . . Inspiring Smaller Products," in Actuators 2006, 10th International Conference on New Actuators, vol. 50, Jun. 2006, p. 10.

L. Tsai, Robot analysis: the mechanics of serial and parallel manipulators. Wiley-Interscience, 1999.

R. Balachandran, J. Mitchell, B. Dawant, and J. Fitzpatrick, "Accuracy evaluation of microTargeting Platforms for deep-brain stimulation using virtual targets," IEEE Transactions on Biomedical Engineering, vol. 56, No. 1, pp. 37-44, Jan. 2009.

S.E. Salcudean, P.A. Drexel, D Ben-Dov, A.J. Taylor, and P.D. Lawrence, "A six degree-of-freedom, hydraulic, one person motion simulator," IEEE Intl Conf Rob and Autom, 2437-2443, 1994.

RC Merkle "A new family of six degrees of freedom positional devices" Nanotech. 8 47-52, 1997.

L. Jones, J.-F. Dagenais, W. Danner, and D. Maisonnier, "Design of the Intersector Welding Robot for vacuum vessel assembly and maintenance," Fusion Eng. & Design v51-52 pp. 979-983, 2000.

M. Shoham, et al., "Robotic assisted spinal surgery" Computer Aided Surgery, 12(2) 105-115, 2007.

FM Warren, R Balachandran, JM Fitzpatrick, RF Labadie, "Percutaneous Cochlear Access Using Bone-Mounted, Customized Drill Guides: Demonstration of Concept In-Vitro," Otol.&Neurotol.,2007, 28(3):325-29.

J.B. West, J.M. Fitzpatrick, S. Toms, C.R. Maurer Jr, and R.J. Maciunas, "Fiducial point placement and the accuracy of point-based, rigid body registration," Neurosurgery v.48, pp. 810-817, 2001.

\* cited by examiner

APPARATUS AND METHODS FOR PERCUTANEOUS COCHLEAR IMPLANTATION

CROSS-REFERENCE TO RELATED PATENT APPLICATION

This application claims the benefit, pursuant to 35 U.S.C. §119(e), of U.S. provisional patent application Ser. No. 61/358,579, filed on Jun. 25, 2010, entitled "A BONE-ATTACHED PARALLEL ROBOT FOR PERCUTANEOUS COCHLEAR IMPLANTATION, MECHATRONIC MICROTABLE AND APPLICATIONS OF SAME," by Robert F. Labadie et al., which is incorporated herein by reference in its entirety.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference. In terms of notation, hereinafter, "[n]" represents the nth reference cited in the reference list. For example, "[11]" represents the 11th reference cited in the reference list, namely, [11] R. Labadie, J. Mitchell, R. Balachandran, and J. Fitzpatrick, International Journal of Computer Assisted Radiology and Surgery, vol. 4, no. 3, pp. 273-280, 2009.

STATEMENT OF FEDERALLY-SPONSORED RESEARCH

This invention was made with government support under Grant Nos. R01DC008408 and R01DC010184 awarded by the National Institute of Health—National Institute on Deafness and Other Communication Disorders. The government has certain rights in the invention.

FIELD OF THE INVENTION

The present invention relates generally to a method of percutaneous cochlear implantation, and more particularly to a method of percutaneous cochlear implantation using a mechatronic microtable.

BACKGROUND

Accuracy and precision are paramount concerns for minimally-invasive surgeries targeting small structures embedded in surrounding tissue. Stereotactic frames are used to locate physical targets identified on medical images or anatomical atlases, and have been in clinical use for over fifty years. However, they are not used in applications requiring sub-millimetric accuracy, including cochlear implant surgery. In these cases, rigid, non-adjustable frame systems attached directly to the bone are favored, in view of their superior accuracy. The major drawback of using existing microstereotactic frame is the time delay associated with its manufacturing. The only current commercially available option, the STarFix™ (FHC, Inc., Bowdoin, Me.) requires a delay of several days—in the middle of the surgical procedure—for off-site manufacturing.

Therefore, a heretofore unaddressed need exists in the art to address the aforementioned deficiencies and inadequacies.

SUMMARY OF THE INVENTION

The present invention, in one aspect, relates to a method of percutaneous cochlear implantation (PCI). In one embodiment, the method includes the steps of (a) implanting a plurality of anchor members in a skull of a patient surrounding an ear of the patient, (b) attaching a docking frame to the plurality of anchor members, wherein the docking frame has (i) a docking platform with a central through hole adapted for allowing access to the ear during a PCI, and (ii) a plurality of fiducial members protruding from a top surface of the docking platform, (c) acquiring a computed-tomography (CT) image of an area of the patient's head including the ear and the plurality of fiducial members, (d) determining a centroid of each of the plurality of fiducial members and a trajectory for a PCI according to the CT image, (e) configuring a parallel robot by a computer processor according to the CT image, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform having a central through hole adapted for allowing the one or more surgical tools to pass therethrough during the PCI, and wherein the computer processor is programmed to set each of the plurality of linear actuators such that the top platform is aligned with the trajectory with respect to the centroids of the plurality of fiducial members to be received by the corresponding plurality of receiving mechanism, (f) attaching the configured parallel robot to the docking frame such that each of the plurality of fiducial members is received by a respective receiving mechanism in the base platform of the parallel robot, and (g) performing the PCI using the one or more surgical tools received by the top platform of the parallel robot.

In one embodiment, the plurality of anchor members includes three anchor members.

In one embodiment, the plurality of fiducial members includes three fiducial members.

In one embodiment, each of the plurality of fiducial members has at least a partial spherical shape.

In one embodiment, each of the plurality of fiducial members is made of titanium.

In one embodiment, the docking platform is made of aluminum or carbon fiber.

In another embodiment, the plurality of linear actuators includes six linear actuators mounted in pairs to the base platform of the parallel robot and crossing over to three mounting points on the top platform of the parallel robot.

In yet another embodiment, the parallel robot is adapted for affording six or four degrees of freedom when the parallel robot is being configured.

In a further embodiment, the parallel robot is adapted such that the top platform of the parallel robot can be aligned with the trajectory with a precision better than about 0.9 mm.

In another aspect, the present invention relates to an apparatus for PCI. In one embodiment, the apparatus includes (a) a docking frame adapted for being attachable to a plurality of anchor members implanted in a skull of a patient surrounding an ear of the patient, wherein the docking frame has a docking platform and a plurality of fiducial members protruding from a top surface of the docking platform, the docking platform having a central through hole adapted for allowing access to the ear when the docking frame is attached to the plurality of anchor members for a PCI, and (b) a parallel robot mounted on the docking frame, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member of the docking frame, each of the top platform and the base platform having a central through hole adapted for allowing the one or more surgical tools to pass therethrough during the PCI. The parallel robot is configurable by a computer processor according to a CT image acquired when the docketing frame is attached to the plurality of anchor members implanted in the skull of the patient. the CT image includes an image of an area of the patient's head including the ear and the plurality of fiducial members. The computer processor is programmed to (i) determine a centroid of each of the plurality of fiducial members and a trajectory for the PCI according to the CT image, and (ii) set each of the plurality of linear actuators of the parallel robot such that the top platform of the parallel robot is aligned with the trajectory with respect to the centroids of the plurality of fiducial members. In several embodiments of the present invention, such an apparatus takes the form of a mechatronic microtable.

In one embodiment, the plurality of anchor members comprises three anchor members.

In one embodiment, the plurality of fiducial members comprises three fiducial members.

In one embodiment, each of the plurality of fiducial members has at least a partial spherical shape.

In another embodiment, each of the plurality of fiducial members is made of titanium.

In yet another embodiment, the docking platform is made of aluminum or carbon fiber.

In a further embodiment, the plurality of linear actuators includes six linear actuators mounted in pairs to the base platform of the parallel robot and crossing over to three mounting points on the top platform of the parallel robot.

In yet another aspect, the present invention relates to a method of performing an intracranial surgery. In one embodiment, the method includes the steps of (a) implanting three or more anchor members in a skull of a patient, (b) attaching a docking frame to the three or more anchor members, wherein the docking frame has (i) a docking platform with a central through hole adapted for allowing access to an area of the patient's brain under surgery, and (ii) three or more fiducial members protruding from a top surface of the docking platform, (c) acquiring a CT image of the area of the patient's brain including the three or more fiducial members, (d) determining a centroid of each of the three or more fiducial members and a trajectory for the intracranial surgery according to the CT image, (e) configuring a parallel robot by a computer processor according to the CT image, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform having a central through hole adapted for allowing the one or more surgical tools to pass therethrough during the intracranial surgery, and wherein the computer processor is programmed to set each of the plurality of linear actuators such that the top platform is aligned with the trajectory with respect to the centroids of the plurality of fiducial members to be received by the corresponding plurality of receiving mechanisms, (f) attaching the configured parallel robot to the docking frame such that each of the three or more fiducial members is received by a respective receiving mechanism in the base platform of the parallel robot, and (g) performing the intracranial surgery using the one or more surgical tools received by the top platform of the parallel robot.

In one embodiment, each of the three or more fiducial members has at least a partial spherical shape.

In another embodiment, each of the three or more fiducial members is made of titanium.

In yet another embodiment, the docking platform is made of aluminum or carbon fiber.

In a further embodiment, the plurality of linear actuators comprises six linear actuators mounted in pairs to the base platform of the parallel robot and crossing over to three mounting points on the top platform of the parallel robot.

These and other aspects of the present invention will become apparent from the following description of the preferred embodiment taken in conjunction with the following drawings and their captions, although variations and modifications therein may be affected without departing from the spirit and scope of the novel concepts of the disclosure.

DETAILED DESCRIPTION

Figure 1:
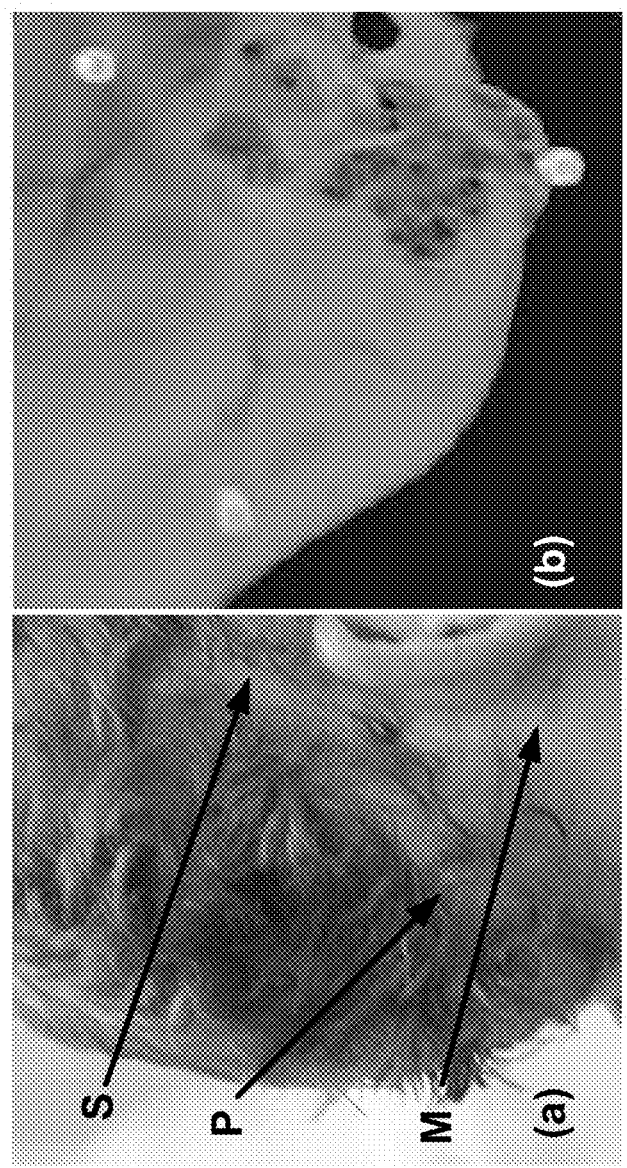
FIG. 1 shows (a) three anchors implanted in the bone surrounding an ear of a patient, and (b) a scout view of a computed tomography (CT) image showing the three anchors in (a).

The present invention is more particularly described in the following examples that are intended as illustrative only since numerous modifications and variations therein will be apparent to those skilled in the art. Various embodiments of the invention are now described in detail. Referring to the drawings, FIGS. 1-12, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, if any, the term "computed tomography (CT)" or x-ray computed tomography refers to a medical imaging method employing tomography created by computer processing. Digital geometry processing is used to generate a three-dimensional image of the inside of an object from a large series of two-dimensional X-ray images taken around a single axis of rotation. CT produces a volume of data that can be manipulated, through a process known as "windowing", in order to demonstrate various bodily structures based on their ability to block the X-ray beam. Although historically the images generated were in the axial or transverse plane, orthogonal to the long axis of the body, modern scanners allow this volume of data to be reformatted in various planes or even as volumetric representations of structures.

As used herein, if any, the term "parallel robot" or parallel manipulator refers to an articulated robot that uses similar mechanisms for the movement of one or more manipulator arms. Their "parallel" distinction, as opposed to a serial manipulator, is that the end effector (or "hand") of this linkage (or "arm") is connected to its base by a number of (usually three or six) separate and independent linkages working in parallel. "Parallel" is used here in the topological sense, rather than the geometrical; these linkages act together, but it is not implied that they are aligned as parallel lines. As an example, a Stewart or Gough-Stewart parallel robot is a type of parallel robot that incorporates six prismatic or linear actuators. These actuators are mounted in pairs to the mechanism's base, crossing over to three mounting points on a top plate. Devices placed on the top plate can be moved in the six degrees of freedom in which it is possible for a freely-suspended body to move. These are the three linear movements x, y, z (lateral, longitudinal and vertical), and the three rotations pitch, roll, and yaw. Because the device has six linear actuators, it is also known as a hexapod.

As used herein, "plurality" means two or more.

As used herein, the terms "comprising," "including," "carrying," "having," "containing," "involving," and the like are to be understood to be open-ended, i.e., to mean including but not limited to.

OVERVIEW OF THE INVENTION

To increase efficacy of therapy delivery and prevent injury to nerves, arteries, brain tissue and other delicate structures during minimally invasive intracranial surgeries, it is desirable to design devices that exceed the positioning accuracy of traditional stereotactic frames. Microsterotactic frames (i.e. bone-attached rigid fixtures custom-made for each patient) are capable of high accuracy, but require manufacturing delays. Repurposing a strategy originally developed for knee arthroplasty and spinal procedures, a method to streamline clinical workflow by replacing the microstereotactic frame with a mechatronic microtable including a miniature parallel robot, referred herein as an automated image-guided microstereotactic (AIM) frame, is described according to various embodiments of the invention. The AIM frame concept is illustrated by addressing percutaneous cochlear implantation (PCI) surgery. The AIM frame can be seamlessly integrated into the surgical and technological workflow of PCI.

Previously, several researchers have demonstrated the efficacy of bone-attached robots for establishing a fixed relationship between a robot's coordinate frame and a surgical target. Plaskos et al. [1], Song et al. [2], and Wolf et al. [3], have designed bone-attached parallel robots for knee arthroplasty. Similarly, the Mazor SpineAssist robot [4] is a commercially available bone-attached parallel robot designed for pedicle screw placement in the spine.

Both [3] and [5] use variations of the Gough-Stewart parallel robot architecture, which provides six degrees of freedom, and has been widely studied and previously applied to industrial applications ranging from robotic milling to telescope mirror positioning [6]. Parallel robots have been favored for bone-attached surgery due to their stiffness, high payload-to-weight ratio, and potential for high positioning accuracy.

In this disclosure, cochlear implant (CI) surgery is addressed as an example to illustrate the AIM frame approach to high-accuracy intracranial targeting. Cochlear implants are electronic devices that can restore a sense of hearing to individuals who have severe or total hearing loss. In a cochlear implant system, an external microphone and sound/speech processing unit transmits signals through the skin to a subcutaneous receiver, which applies electrical impulses to an electrode array implanted inside the cochlea, stimulating the nearby auditory nerve.

The current procedure for CI surgery requires removal of temporal bone through a process called mastoidectomy, using a hand-operated drill to gain access to the cochlea, which is located at a depth of approximately 35 mm. During drilling, several sensitive anatomical features embedded in the bone must be identified and preserved. These include the facial nerve, damage to which can result in permanent ipsilateral facial paralysis, and a nerve called the chorda tympani which controls taste sensation on the ipsilateral tip of the tongue. These two nerves are separated by approximately 2 mm at the facial recess, through which the electrode array must pass. To prevent injury, the surgeon must relate a three-dimensional mental map of critical subsurface features to anatomical landmarks exposed during drilling, relying on hand-eye coordination and memory to avoid cutting these nerves or encroaching on the ear canal (which can lead to infection).

Figure 2:
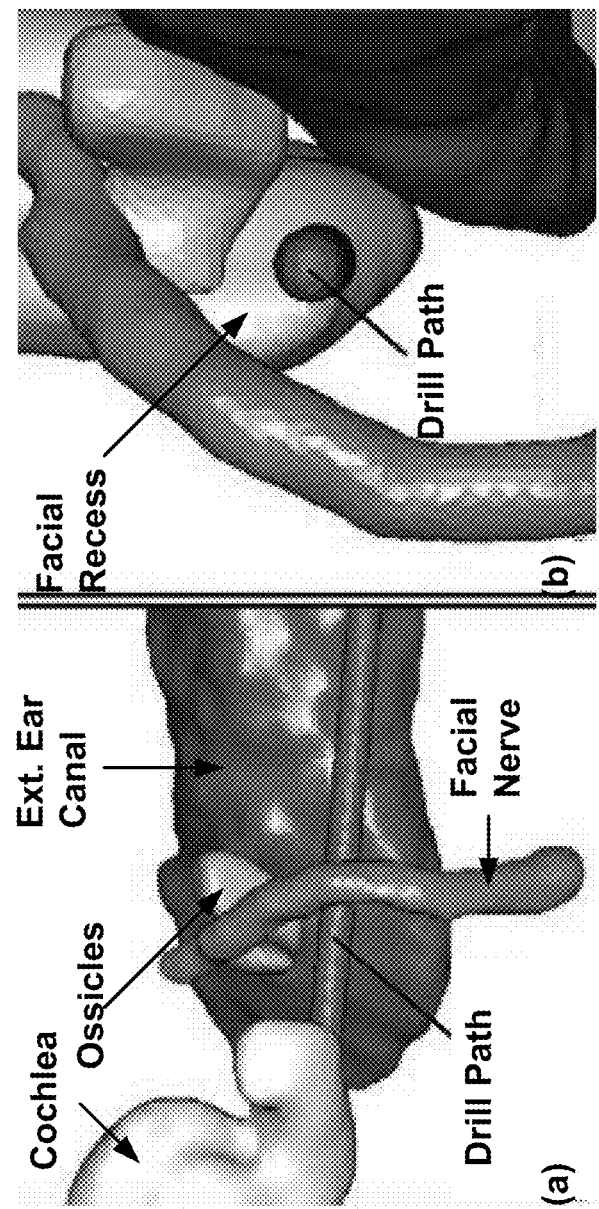
FIG. 2 shows a planned drill path for a right ear through (a) a view from posterior to anterior and (b) a view through a facial recess.
Figure 3:
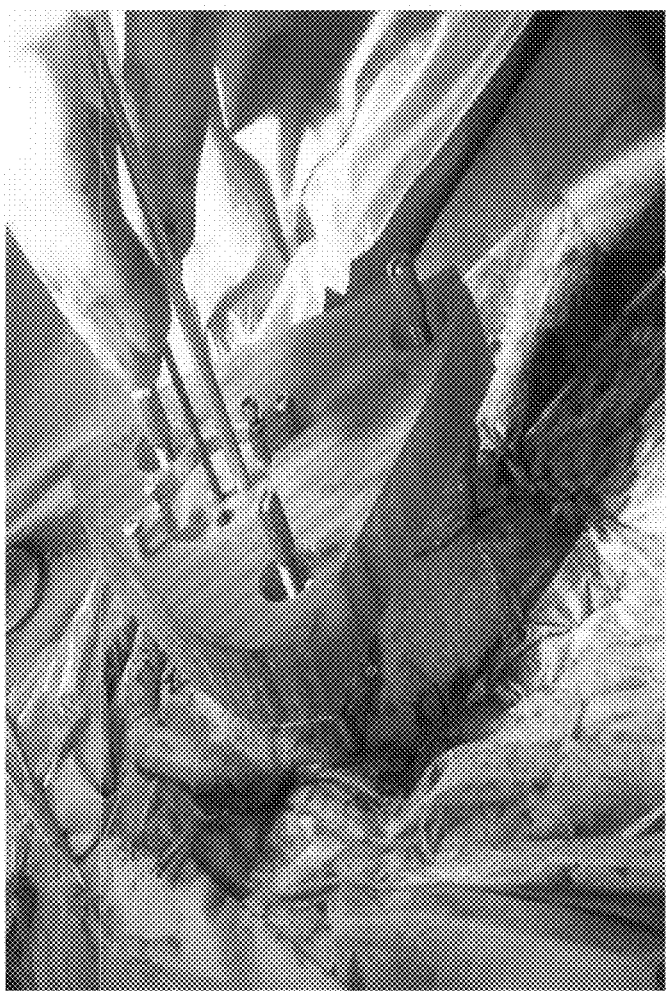
FIG. 3 shows a microtable mounted on a patient's skull around the patient's ear. The microtable is used in a conventional percutaneous cochlear implantation (PCI) procedure.

In recent years, a minimally-invasive technique called percutaneous cochlear implantation (PCI) has been developed to reduce the risks and time required for traditional CI surgery [7], [8]. The procedure utilizes a microstereotactic frame to accurately locate surgical targets. The PCI procedure begins with placement of three self-tapping metal anchors with spherical heads on the temporal bone surrounding an ear of a patient, as shown in FIG. 1(*a*). In one embodiment, the three anchors are implanted at the mastoid (M), posterior (P), and suprahelix (S) locations. A computed tomography (CT) scan of the anchors is acquired and a software is used to automatically localize the centers of the spherical heads and an optimal trajectory to the cochlea is automatically computed from segmented image information [9]. FIG. 1(*b*) shows a scout view of a CT image showing the three anchors. FIG. 2 shows planned drill path for a right ear through (a) a view from posterior to anterior and (b) a view through a facial recess. Next, a bone-attached microstereotactic frame called a microtable (machined from a plate of thermally resistant plastic) is designed to guide and constrain a drill and insertion tool to the planned drill trajectory. Finally, the microtable is fabricated using a computer numeric control (CNC) milling machine near the operating room, sterilized, and attached to the bone anchors as shown in FIG. 3 to serve as a guide for the drill and insertion tool, which lock securely to it. The PCI technique is currently undergoing clinical validation [7]. It is hypothesized that the PCI technique will consistently require approximately 60 minutes to complete (the estimated operative time for CI surgery ranges from 70-150 minutes depending on the experience of the surgeon [10]). A mean drill tip accuracy of 0.37±0.18 mm [11] has been demonstrated. The total time required for fabrication, sterilization, and delivery of each microtable is approximately 30 minutes.

To reduce the total operating time while achieving accuracies similar to those obtained via a microtable, the AIM frame system described in this disclosure uses a sterilizable Gough-Stewart parallel robot mounted on a standardized, rigid, pre-positioning frame.

The present invention, in one aspect, relates to a method of percutaneous cochlear implantation (PCI). In one embodiment, the method includes the steps of (a) implanting a plurality of anchor members in a skull of a patient surrounding an ear of the patient, (b) attaching a docking frame to the plurality of anchor members, wherein the docking frame has (i) a docking platform with a central through hole adapted for allowing access to the ear during a PCI, and (ii) a plurality of fiducial members protruding from a top surface of the docking platform, (c) acquiring a computed-tomography (CT) image of an area of the patient's head including the ear and the plurality of fiducial members, (d) determining a centroid of each of the plurality of fiducial members and a trajectory for a PCI according to the CT image, (e) configuring a parallel robot by a computer processor according to the CT image, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform having a central through hole adapted for allowing the one or more surgical tools to pass therethrough during the PCI, and wherein the computer processor is programmed to set each of the plurality of linear actuators such that the top platform is aligned with the trajectory with respect to the centroids of the plurality of fiducial members to be received by the corresponding plurality of receiving mechanism, (f) attaching the configured parallel robot to the docking frame such that each of the plurality of fiducial members is received by a respective receiving mechanism in the base platform of the parallel robot, and (g) performing the PCI using the one or more surgical tools received by the top platform of the parallel robot.

In one embodiment, the plurality of anchor members includes three anchor members.

In one embodiment, the plurality of fiducial members includes three fiducial members.

In one embodiment, each of the plurality of fiducial members has at least a partial spherical shape.

In one embodiment, each of the plurality of fiducial members is made of titanium.

In one embodiment, the docking platform is made of aluminum or carbon fiber.

In another embodiment, the plurality of linear actuators includes six linear actuators mounted in pairs to the base platform of the parallel robot and crossing over to three mounting points on the top platform of the parallel robot.

In yet another embodiment, the parallel robot is adapted for affording six or four degrees of freedom when the parallel robot is being configured.

In a further embodiment, the parallel robot is adapted such that the top platform of the parallel robot can be aligned with the trajectory with a precision better than about 0.9 mm.

In another aspect, the present invention relates to an apparatus for PCI. In one embodiment, the apparatus includes (a) a docking frame adapted for being attachable to a plurality of anchor members implanted in a skull of a patient surrounding an ear of the patient, wherein the docking frame has a docking platform and a plurality of fiducial members protruding from a top surface of the docking platform, the docking platform having a central through hole adapted for allowing access to the ear when the docking frame is attached to the plurality of anchor members for a PCI, and (b) a parallel robot mounted on the docking frame, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member of the docking frame, each of the top platform and the base platform having a central through hole adapted for allowing the one or more surgical tools to pass therethrough during the PCI. The parallel robot is configurable by a computer processor according to a CT image acquired when the docketing frame is attached to the plurality of anchor members implanted in the skull of the patient. the CT image includes an image of an area of the patient's head including the ear and the plurality of fiducial members. The computer processor is programmed to (i) determine a centroid of each of the plurality of fiducial members and a trajectory for the PCI according to the CT image, and (ii) set each of the plurality of linear actuators of the parallel robot such that the top platform of the parallel robot is aligned with the trajectory with respect to the centroids of the plurality of fiducial members.

In one embodiment, the plurality of anchor members comprises three anchor members.

In one embodiment, the plurality of fiducial members comprises three fiducial members.

In one embodiment, each of the plurality of fiducial members has at least a partial spherical shape.

In another embodiment, each of the plurality of fiducial members is made of titanium.

In yet another embodiment, the docking platform is made of aluminum or carbon fiber.

In a further embodiment, the plurality of linear actuators includes six linear actuators mounted in pairs to the base platform of the parallel robot and crossing over to three mounting points on the top platform of the parallel robot.

In a further aspect, the present invention relates to a method of performing an intracranial surgery. In one embodiment, the method includes the steps of (a) implanting three or more anchor members in a skull of a patient, (b) attaching a docking frame to the three or more anchor members, wherein the docking frame has (i) a docking platform with a central through hole adapted for allowing access to an area of the patient's brain under surgery, and (ii) three or more fiducial members protruding from a top surface of the docking platform, (c) acquiring a CT image of the area of the patient's brain including the three or more fiducial members, (d) determining a centroid of each of the three or more fiducial members and a trajectory for the intracranial surgery according to the CT image, (e) configuring a parallel robot by a computer processor according to the CT image, wherein the parallel robot has a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform having a central through hole adapted for allowing the one or more surgical tools to pass therethrough during the intracranial surgery, and wherein the computer processor is programmed to set each of the plurality of linear actuators such that the top platform is aligned with the trajectory with respect to the centroids of the plurality of fiducial members to be received by the corresponding plurality of receiving mechanisms, (f) attaching the configured parallel robot to the docking frame such that each of the three or more fiducial members is received by a respective receiving mechanism in the base platform of the parallel robot, and (g) performing the intracranial surgery using the one or more surgical tools received by the top platform of the parallel robot.

In one embodiment, each of the three or more fiducial members has at least a partial spherical shape.

In another embodiment, each of the three or more fiducial members is made of titanium.

In yet another embodiment, the docking platform is made of aluminum or carbon fiber.

In a further embodiment, the plurality of linear actuators comprises six linear actuators mounted in pairs to the base platform of the parallel robot and crossing over to three mounting points on the top platform of the parallel robot.

Additional details are set forth below.

EXAMPLE 1

Figure 4:
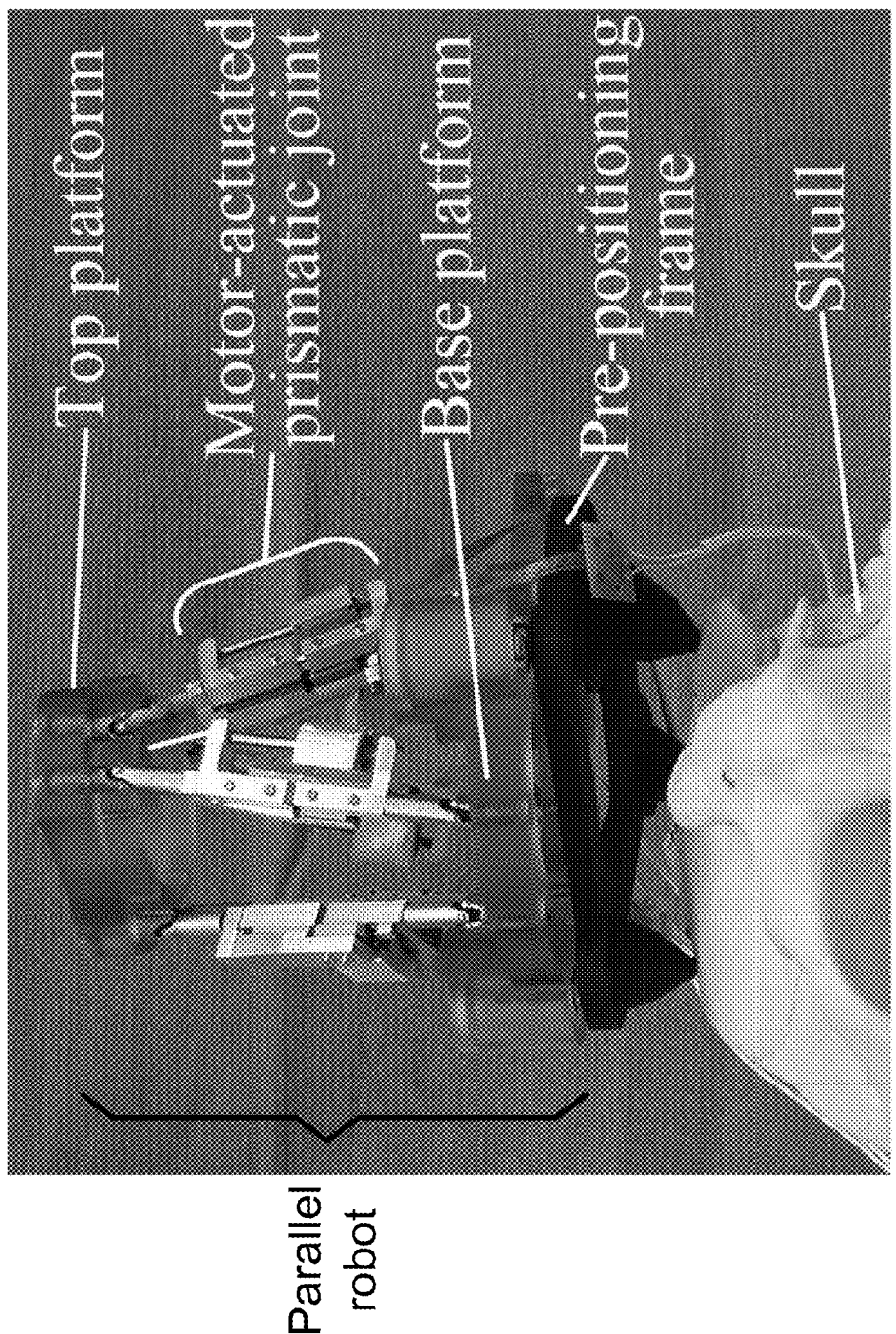
FIG. 4 shows a mechatronic microtable attached to a human skull according to one embodiment of the present invention.

FIG. 4 shows an AIM frame attached to a human skull according to one embodiment of the present invention. The AIM frame has a rigid pre-positioning frame, also referred herein as a docking frame, that is mounted to the skull with surgical screws, a robot that attaches to titanium spheres on the pre-positioning frame, and an electronic equipment enclosure. The robot has a top platform and a bottom platform. Both the base platform of the robot and the pre-positioning frame have large holes through their centers to allow the surgical tools (drill and cochlear implant insertion tool) to pass through to the target.

Both the top platform and base platform of the AIM frame are milled from polyetherimide, an autoclavable thermoplastic that maintains high rigidity and tensile strength at high temperatures. The joints and all fasteners are made of autoclavable metals. The pre-positioning frame is made from an autoclavable polyetherimide or acrylonitrile butadiene styrene (ABS). It is understood that other materials can also be used for the top platform, the base platform, and the pre-positioning frame.

A. Pre-Positioning Frame

Figure 5:
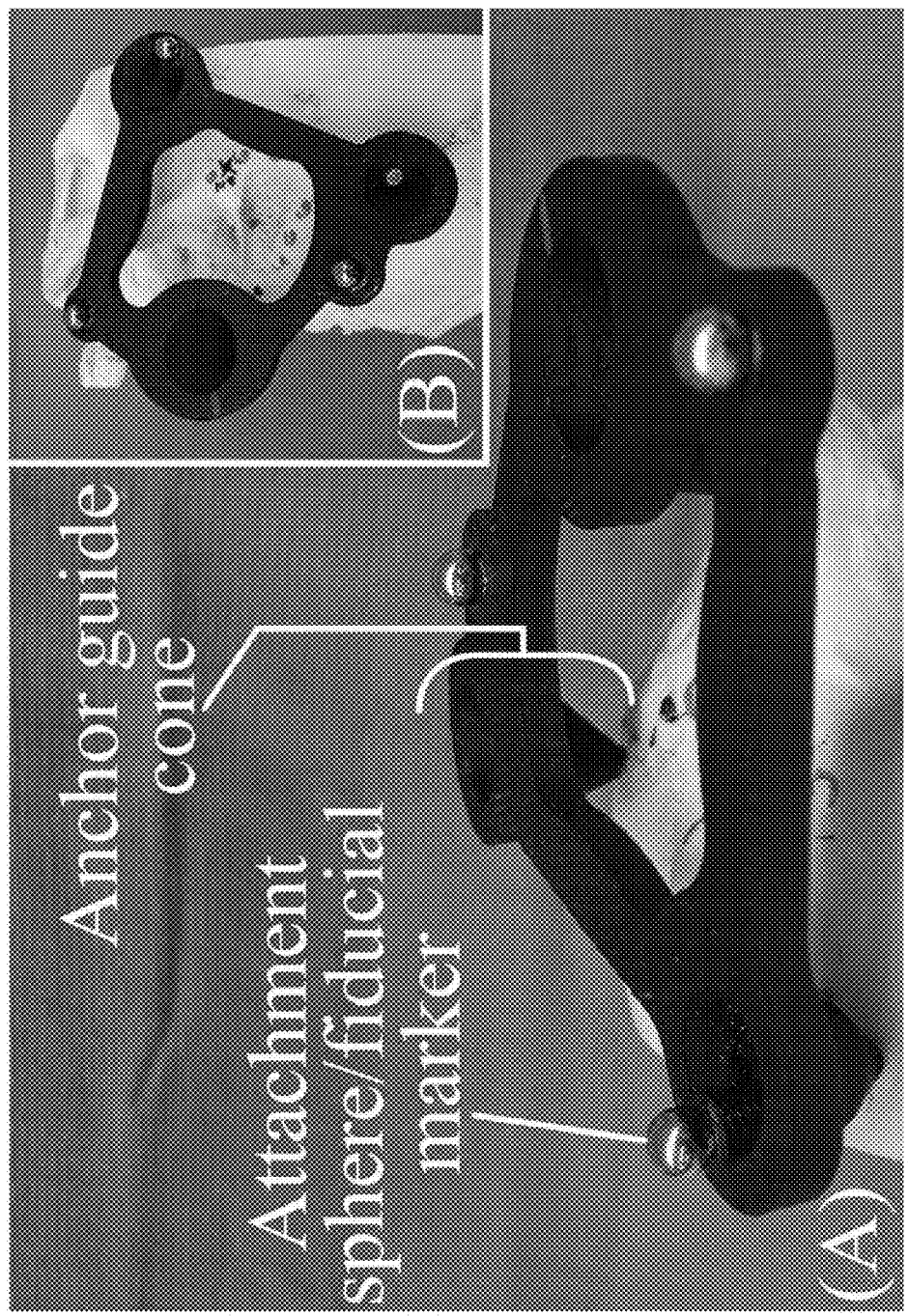
FIG. 5 shows (a) an oblique view and (b) a top view of a docking frame attached to a human skull as part of the mechatronic microtable shown in FIG. 4, according to one embodiment of the present invention.

FIG. 5 shows a pre-positioning frame according to one embodiment of the present invention. The pre-positioning frame serves at least three functions. First, it acts as a template to guide the surgeon to insert the bone anchors at the appropriate locations and orientations (perpendicular to the bone surface). Second, the spheres on the top of the pre-positioning frame act as fiducial markers for registering CT images to the robot's coordinate frame. Third, the pre-positioning frame orients the robot such that when it is attached and in its nominal position (with all actuators at equal lengths), it will be as close as possible to the statistically expected drill trajectory, based on actual drill trajectories in prior clinical validation studies (see FIG. 6). This aligns the robot's workspace as closely as possible to the necessary workspace, minimizing the distance each actuator must travel to reach the space of possible desired trajectories, allowing the robot to be as small and light as possible. The robot itself attaches to the fiducial marker spheres on top of the prepositioning frame, using the gripping mechanism described in [11].

Figure 6:
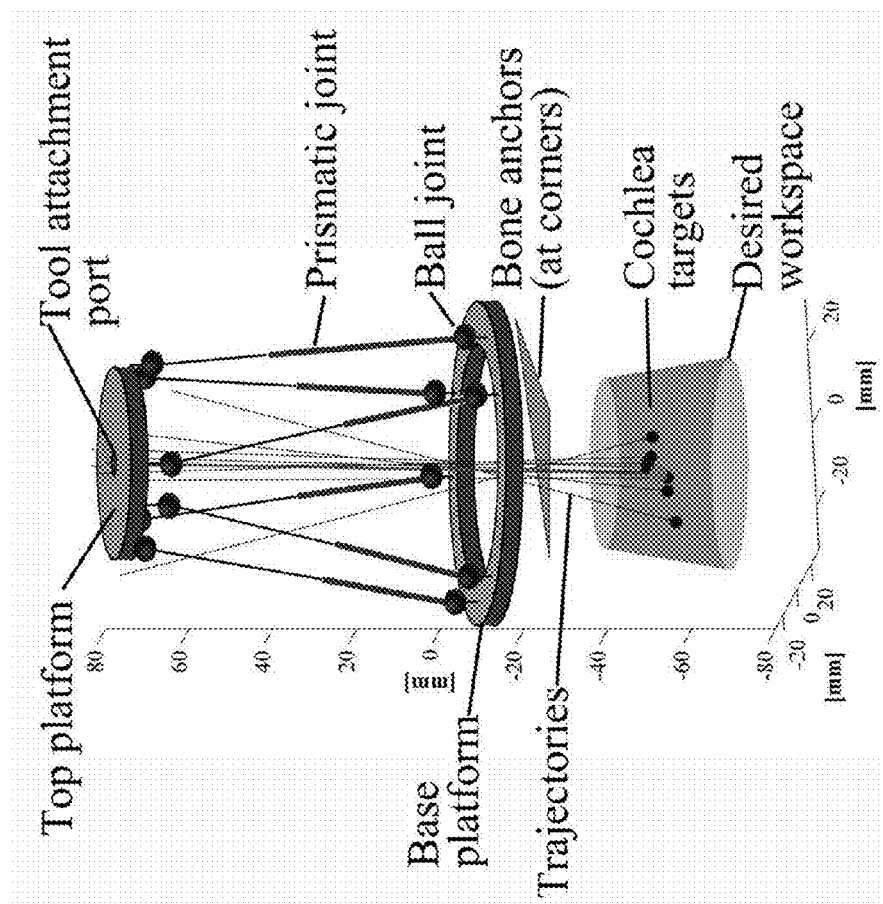
FIG. 6 shows a schematic diagram of a parallel robot, according to one embodiment of the present invention. PCI trajectories from actual clinical data are also shown.
Figure 7:
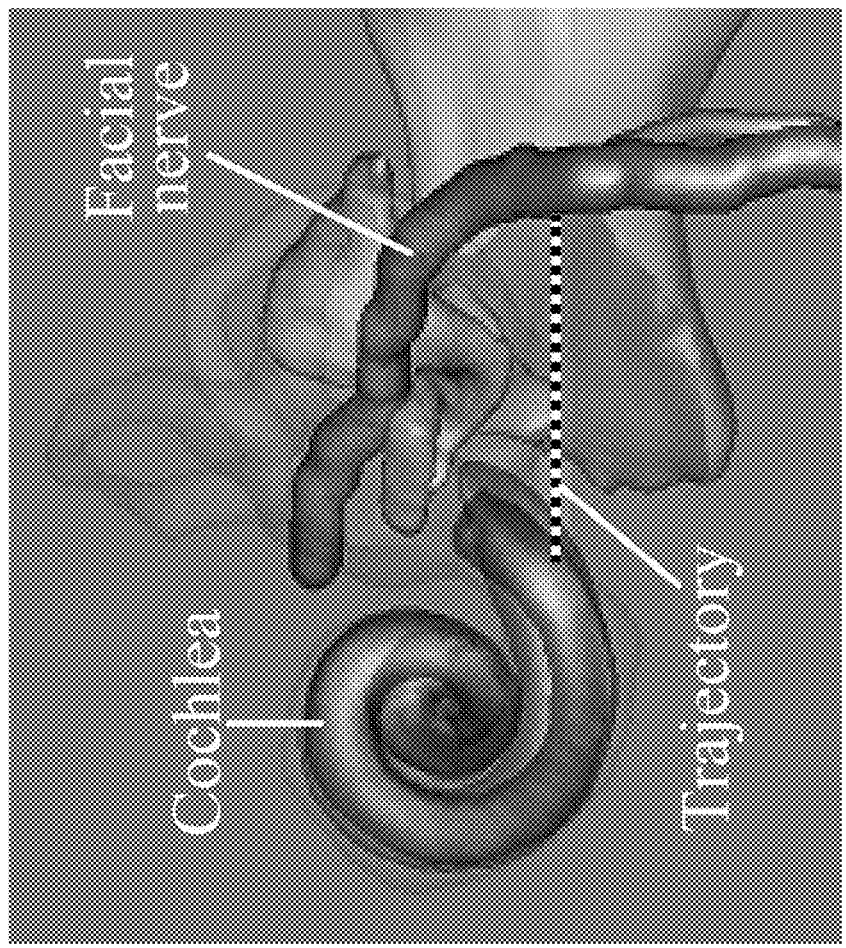
FIG. 7 shows a computer rendering of segmented structures along with a planned trajectory to a cochlea target for a PCI.

To design the pre-positioning frame for the AIM frame for PCI, an analysis of PCI trajectories from a sample of eight prior microtable clinical trials is performed. These trajectories were planned using the algorithm of Noble, et al. [9], which performs automatic segmentation of temporal bone CT scans to identify important anatomical structures and determine an optimal trajectory that avoids the facial nerve and accesses the cochlea. A computer rendering of the segmented structures along with a planned trajectory is shown in FIG. 7. The prepositioning frame was designed to align the nominal position of the robot with the vector from the mean entry point to the mean target point in the eight clinical trials. FIG. 6 depicts the eight desired trajectories from the sample of PCI clinical data, in a coordinate system placed at the center of the base frame of the AIM frame prototype mounted on the pre-positioning frame. The robot is shown in its nominal, unadjusted pose, where the tool attachment port on the top platform is centrally located with respect to the PCI trajectories.

B. Gough-Stewart Platform

FIG. 6 shows a schematic diagram of a parallel robot as part of the mechatronic microtable shown in FIG. 4, according to one embodiment of the present invention. The parallel robot is based on a 6-6 Gough-Stewart parallel robot architecture, consisting of two platforms connect by six actuated prismatic joints. The ends of each prismatic joint are connected to passive ball joints, arranged to form the vertices of a semi-regular hexagon on each platform. This robot design was selected for ease of application, since there is a large body of existing literature describing it and its inverse kinematics are well-understood.

While the six degrees of freedom afforded by the Gough-Stewart platform are more than strictly necessary (only four degrees of freedom are required for aligning an axisymmetric tool to a trajectory), it may sometimes be valuable to include redundant degrees of freedom, which may be utilized as free parameters for avoiding link collisions, minimization of encoder uncertainty propagation, and avoidance of singularity loci. In other embodiments, the tradeoff between the simplicity of the mechanism (reduction of motors and thereby cost) and the desirability of including redundant degrees of freedom will be explored. Alternate parallel robot designs will also be explored. Properties such as error propagation, stiffness, kinematic conditioning will be compared.

C. Actuators and Sensors

Figure 8:
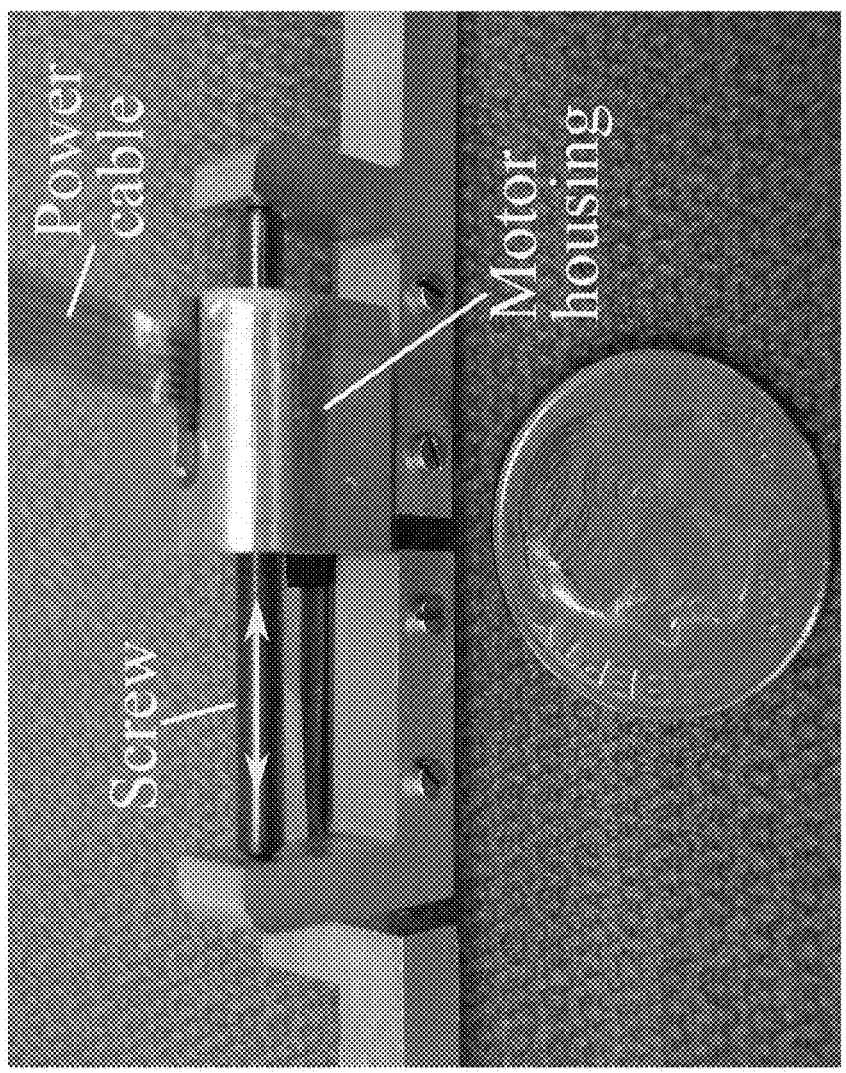
FIG. 8 shows one of the six motor-actuated prismatic joints of a parallel robot, according to one embodiment of the present invention.

FIG. 8 shows one of the six motor-actuated prismatic joints of the parallel robot shown in FIG. 4, according to one embodiment of the present invention. The robot is actuated by six Squiggle SQL 3.4 linear piezoelectric motors (New Scale Technologies; Victor, N.Y.). Each motor consists of a lead screw engaged in a threaded nut. Piezoelectric plates attached to the nut induce ultrasonic standing waves which cause rotation and translation of the lead screw [12]. These motors were chosen for their high power-to-weight ratio, small size, and high resolution of motion. Each motor weighs 1.2 g and can generate bidirectional motion with 2 N maximum output force. The stator package is 3.4 mm×3.4 mm×10 mm. The motors can extend and retract at 4 mm/s while exerting 1 N. It is estimated (conservatively) that the required positioning time for PCI trajectories is under 5 seconds. When the power source is removed, the motors lock and are not back drivable. The suitability of these motors for direct exposure to repeated sterilization is not known, though one motor has been subjected to a standard autoclave sterilization cycle (270.0° F., 4 minutes sterilization time, 1 hour and 13 minutes total cycle time), and another to ethylene oxide gas sterilization (130° F., total cycle time of 14 hours and 59 minutes). Qualitatively, no degradation of performance has been observed for either motor following sterilization.

Each motor is enclosed in a bolted aluminum fixture forming a prismatic joint which may be extended and retracted by the motor, as shown in FIG. 8. The fixture also houses a TRACKER Position Sensor (New Scale Technologies; Victor, N.Y.), a Hall effect-based encoder with a minimum resolution of 0.5 μm. The TRACKER is used for closed-loop control.

D. Control Hardware

Each motor is powered by a separate MC-1100 motor controller (New Scale Technologies; Victor, N.Y.). Each motor controller is connected via a universal serial bus (USB) connection to a USB hub, which in turn connects to a personal computer with a single USB cable. The control electronics (motor control boards and USB hub) are housed in a separate electronics box. The electronics box is connected to the robot with a single, detachable, three-foot cable. Detaching the robot and control cable allows these components to be sterilized (it is not necessary to sterilize the electronics box, since it is sufficiently remote from the patient and can be covered in a plastic bag in the operating room).

E. Control Software

To orient the top platform of the AIM frame to a desired trajectory, the inverse kinematics of the robot are used to determine required joint displacements. For parallel robots, mathematical expressions for inverse kinematics are often quite simple (for a derivation of Gough-Stewart platform inverse kinematics, see [13]).

Custom software written in MATLAB (Mathworks; Natick, Mass.) is used for trajectory generation. Each trajectory is planned as a straight line path from the robot's "home" position to the required position, and uses inverse kinematics to calculate leg lengths at a sequence of closely spaced via points along the trajectory. New Scale Pathway software (New Scale Technologies; Victor, N.Y.) is used to interface with the motor controllers and execute the trajectories. Each motor is independently controlled using a proportional-integral-derivative feedback loop.

F. Surgical Workflow

Figure 9:
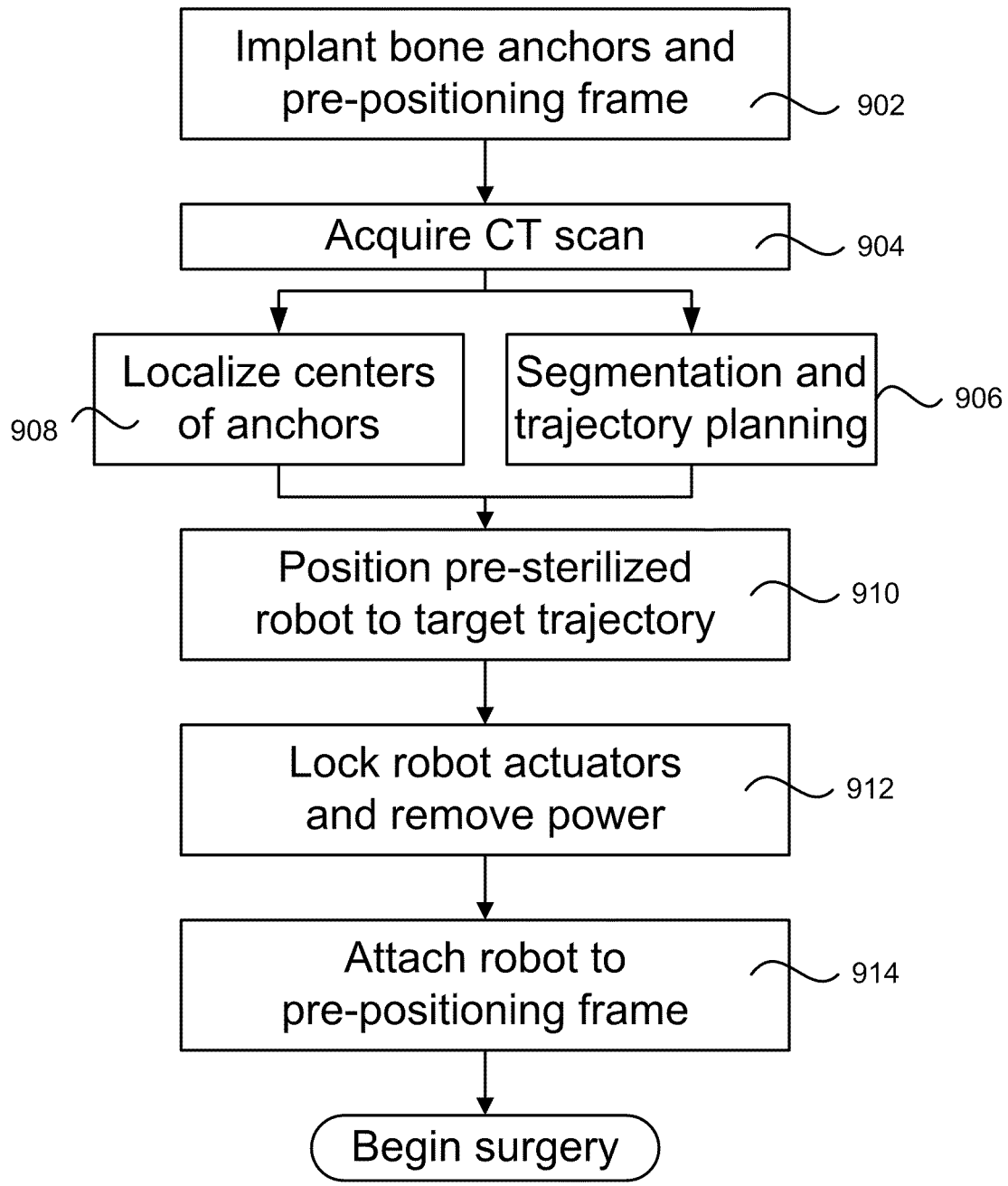
FIG. 9 shows a flow chart illustrating the pre-surgical process for PCI using a mechatronic microtable, according to one embodiment of the present invention.

The AIM frame can fit seamlessly into the clinically-validated PCI surgery process introduced by Labadie et al. [7], with the use of a rapidly-adjustable robot replacing design and fabrication of a microtable. A PCI pre-surgical process modified to include an AIM frame according to one embodiment of the present invention is shown in FIG. 9. First, at step 902, a prepositioning frame designed using prior clinical data is used to guide insertion of three bone screws, which fix the pre-positioning frame to the skull. Next, at step 904 a CT scan allows identification of both patient anatomy and three titanium spheres on top of the pre-positioning frame. Custom software is then used, at steps 906 and 908, to segment critical anatomy, localize the centers of the spheres, and identify a target and trajectory with respect to the sphere locations. At step 910, a miniature Gough-Stewart parallel robot is positioned so that a tool attachment platform on its top platform aligns with the desired trajectory. At step 912, the robot is disconnected from its power source and, at step 914, attached securely to the spheres on top of the pre-positioning frame. After attachment, the robot serves as a locked, microstereotactic frame upon which a surgical drill and cochlear implant insertion tool can be attached during surgery.

In alternative embodiments of the present invention, the positioning accuracy of the AIM frame using the "virtual targets" method introduced by Balachandran et al. [14] will be investigated, with an atlas of cochlea targets obtained from prior microtable clinical trials. Prior to testing, it will be necessary to calibrate the robot to account for manufacturing tolerances. It may also be useful to optimize design parameters of the robot to minimize the propagation of encoder uncertainties to the top platform, although since the encoder resolution is high, it is not yet clear whether this will be necessary. A comprehensive review of calibration and optimization methods relevant to the Gough-Stewart platform may be found in [6]. Alternative parallel robot configurations beyond the Gough-Stewart architecture will also be explored to determine if there may be a structure even better suited to PCI and/or other intracranial procedures.

EXAMPLE 2

Figure 10:
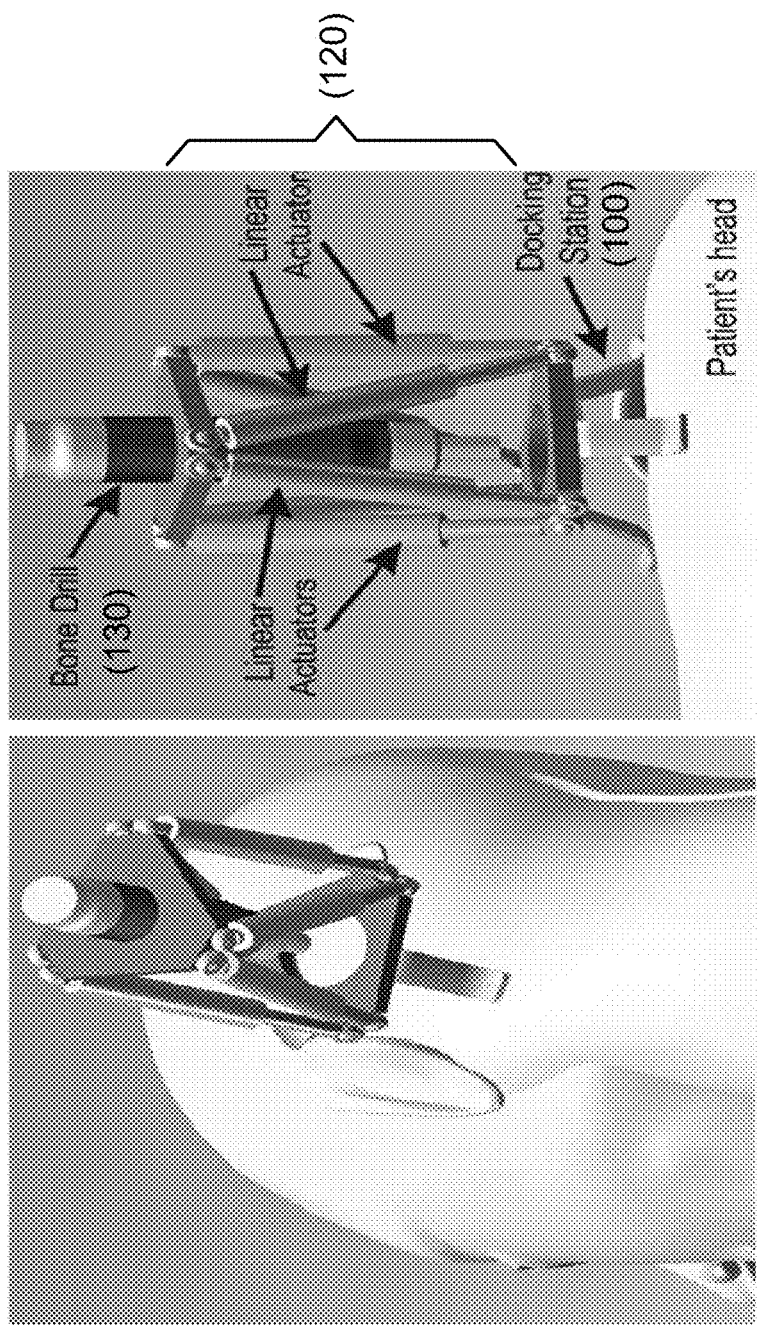
FIG. 10 shows schematically (a) a mechatronic microtable attached to a human skull, and (b) a close-up view of the mechatronic microtable, according to another embodiment of the present invention.

FIG. 10 shows schematically (a) a mechatronic microtable attached to a human skull, and (b) a close-up view of the mechatronic microtable, according to another embodiment of the present invention. The mechatronic microtable comprises a docking frame 100 and a parallel robot 120 mounted on the docking frame 100. The top plate of the parallel robot 120 receives a surgical tool 130 such as a bone drill. Design objectives for the parallel robot are summarized in Table 1.

Figure 11:
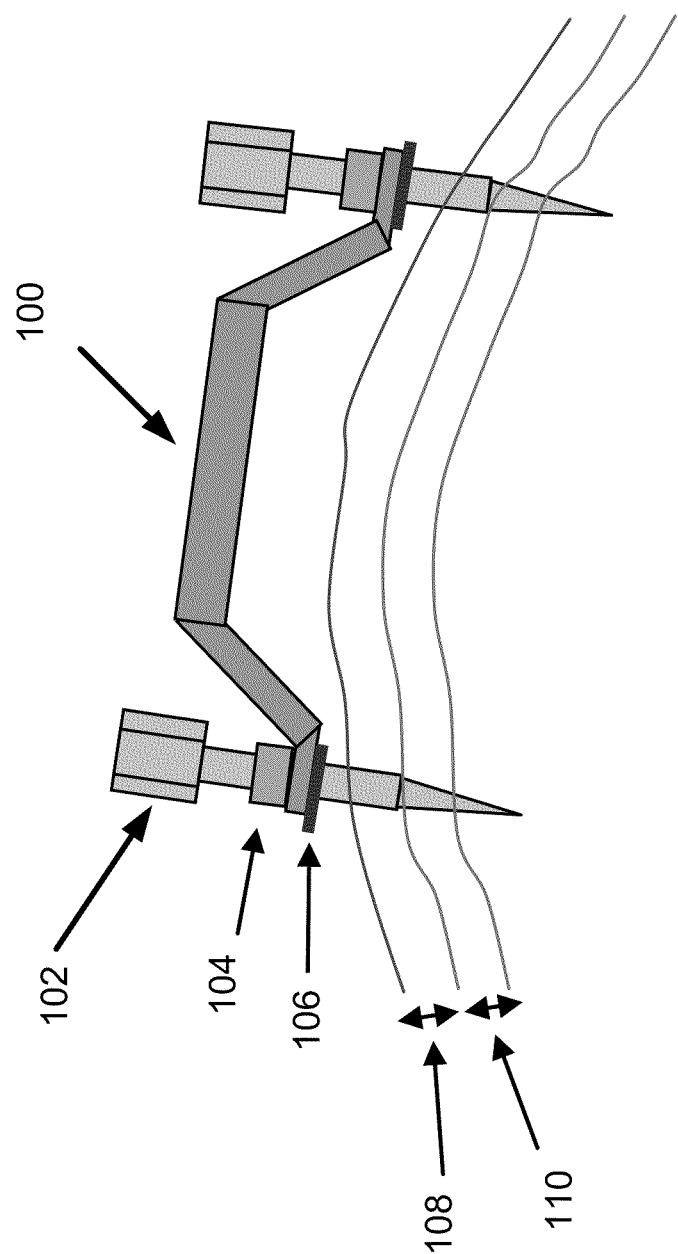
FIG. 11 shows schematically in part a docking frame as part of the mechatronic microtable shown in FIG. 10, according to one embodiment of the present invention.

FIG. 11 shows schematically in part the docking frame 100. Fiducial anchors 102 pass through holes in the docking frame 100 through incisions in the skin 108 and then self-tap into the bone 110. A retaining clip 106 is then slid into one of several grooves in the lower part of each of the fiducial anchors 102, and a nut 104 is tightened. The retaining clip 106 avoids using the pliable skin as platform for the docking frame 100. The top portion of the fiducial anchor 102 is a hexagonal part that serves both to mate with an anchor driver and as a prominent feature for fiducial localization. The anchors 102 are made of a metal, such as titanium, that has high CT attenuation and is compatible with bone. In one embodiment, the docking frame 100 is made of a material, such as aluminum or carbon fiber, that has lower CT attenuation so as to minimize CT imaging artifacts.

After the docking frame 100 is secured via the anchors 102, nuts 104, and retaining clips 106, but before the parallel robot 120 is attached, a CT image is acquired. In that image, the anchors 102 are localized, and the entry and target points are selected.

Figure 12:
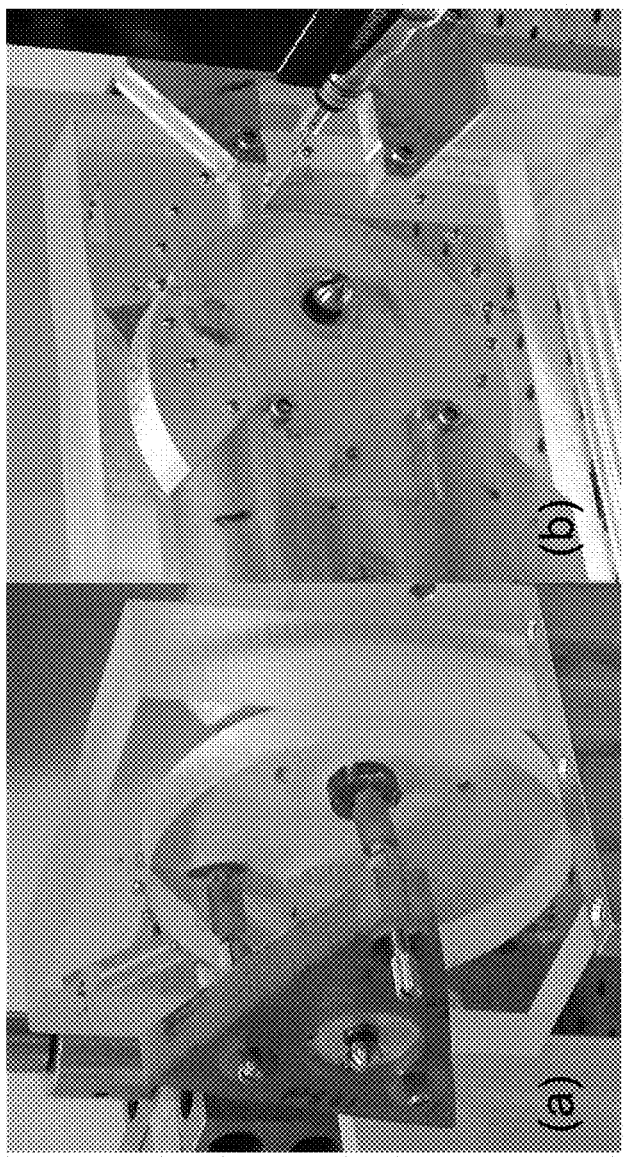
FIG. 12 illustrates phantom testing for determining the accuracy of a microtable, wherein (a) shows a microtable mounted on spherical markers in a phantom, and (b) shows physical localization of spherical markers using the coordinate measuring machine (CMM).

To rigorously test the accuracy of mechatronic microtable, phantom studies are conducted similar to those conducted to test rigid microstereotactic frames [14, 11]. One goal is to measure the accuracy with which the mechatronic microtable places a probe at a specified target using a clinically relevant phantom. Specifically, the placement error, which is defined to be the distance by which a probe (representing the drill) manipulated by the mechatronic microtable approaches its specified target, is estimated. To do this, "virtual targets" is defined in a phantom that is based on geometric relations of the human anatomy of interest. For cochlear implantation, these virtual targets are at the location of the cochlea, approximately 75 mm below the surface of the rigid frame on which the parallel robot is attached. The use of virtual targets eliminates the problem of potential collision between the targeting probe and the target itself, allowing accurate measurement of the placement error. Virtual targets are defined relative to a set of fiducial markers on the phantom, which are used to provide the registration between image and physical space in order to compute the placement error. The location of the probe in physical space is measured to a precision of 0.0055 mm using a coordinate measuring machine (CMM) as shown in FIG. 12.

In one embodiment, an optimized mechatronic microtable is affixed to human cadaveric temporal bone specimens, and proof-of-concept drilling experiments are performed. These experiments are carried out using the procedure that has been successfully applied to prove the concept of PCI using customized microstereotactic frames [19]. Each specimen will undergo fiducial marker placement, as shown in FIG. 1(a). Three abutments for the attachment of fiducial markers will be tapped into the skull, at the mastoid tip, the root of the zygoma, and anterior occiput. These locations are selected to surround the surgical site to increase accuracy [20]. A CT image, as shown in FIG. 1(b), will then be acquired. Planning is carried out to determine drill trajectory, as illustrated in FIG. 2. It will then be confirmed that drill path maintains an adequate margin from vital structures (e.g., facial nerve, horizontal semicircular canal, and floor of middle cranial fossa). The temporal bone will then undergo canal wall up mastoidectomy with facial recess approach. The mechatronic microtable shown in FIG. 10 will then be attached to the bone and a 1-mm diameter drill bit used to drill to the cochlea. At the facial recess, the drill bit will be stopped and photographed digitally. Accuracy will be assessed using photographic images analyzed in a photographic analysis package such as Adobe Illustrator. Measurements will then be taken in pixels with the pixel/mm conversion defined by the 1-mm drill bit. The shortest distance from the edge of the drill bit to the anatomic site of interest (chorda tympani, incudal buttress, facial nerve, and round window) will then be recorded.

In vivo human validation can be also done. Specifically, it can be started by mounting the mechatronic microtable on patients who are having a microtable already constructed. After testing of the microtable, it will be removed and the mechatronic microtable will be tested for accuracy and the speed of each compared.

In summary, an inventive AIM frame for highly accurate minimally invasive intracranial access has been described according to various embodiments of the present invention. A chief clinical advantage of the AIM frame according to various embodiments of the present invention is higher potential accuracy in intracranial procedures, which can be expected to increase efficacy and decrease complication rates. It has the potential to enable many new procedures, such as PCI, that are not approachable with traditional stereotactic frames. Although the AIM frame according to various embodiments of the present invention is discussed in the context of PCI surgery, it is understood that the AIM frame according to various embodiments of the present invention may be utilized to other similar intracranial procedures.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

TABLE 1

| Design Objective | Design Specifications | Reasoning |
| --- | --- | --- |
| Small & Light | 15 cm by 12.5 cm, 1.5 Kg | Small and light enough to be attached as shown in FIG. 10 |
| Workspace | ±25°, 15 mm cube | Sufficient for all 16 successful clinical trials to date |
| Payload | 1 Kg or more | The drill weighs only 0.125 Kg; 1 Kg provides a safety margin |
| Precision | 50 µm, 50 µrad | Providing accuracy substantially equivalent to a rigid microtable |
| Speed | 25 mm/sec | Making required motion achievable in a fraction of a second |
| Sterilizability | Yes | Sterilizable actuators and components are used |

LIST OF REFERENCES

[1] C. Plaskos, P. Cinquin, S. Lavallee, and A. Hodgson, "Praxiteles: a miniature bone-mounted robot for minimal access total knee arthroplasty," Int. J. Med. Robot. Comput. Assist. Surg, vol. 1, no. 4, pp. 67-79, 2005.
[2] S. Song, A. Mor, and B. Jaramaz, "HyBAR: hybrid bone-attached robot for joint arthroplasty," The International Journal of Medical Robotics and Computer Assisted Surgery, vol. 5, no. 2, 2009.
[3] A. Wolf, B. Jaramaz, B. Lisien, and A. DiGioia, "MBARS: mini boneattached robotic system for joint arthroplasty," Int. J. Med. Robot. Comp. Assist. Surg, vol. 1, no. 2, pp. 101-121, 2005.
[4] W. Sukovich, S. Brink-Danan, and M. Hardenbrook, "Miniature robotic guidance for pedicle screw placement in posterior spinal fusion: early clinical experience with the SpineAssist®," The International Journal of Medical Robotics and Computer Assisted Surgery, vol. 2, no. 2, pp. 114-122, 2006.
[5] L. Joskowicz, R. Shamir, M. Freiman, M. Shoham, E. Zehavi, F. Umansky, and Y. Shoshan, "Image-guided system with miniature robot for precise positioning and targeting in keyhole neurosurgery," Computer Aided Surgery, vol. 11, no. 4, pp. 181-193, 2006.
[6] J. Merlet, Parallel robots. Springer-Verlag New York Inc, 2006.
[7] R. Labadie, R. Balachandran, J. Mitchell, J. Noble, O. Majdani, D. Haynes, M. Bennett, B. Dawant, and J. Fitzpatrick, "Clinical Validation Study of Percutaneous Cochlear Access Using Patient-Customized Microstereotactic Frames," Otology & Neurotology, vol. 31, no. 1, p. 94, 2010.
[8] R. Balachandran, J. Mitchell, G. Blachon, J. Noble, B. Dawant, J. Fitzpatrick, and R. Labadie, "Percutaneous cochlear implant drilling via customized frames: An in vitro study," Otolaryngology-Head and Neck Surgery, vol. 142, no. 3, pp. 421-426, 2010.
[9] J. Noble, F. Warren, R. Labadie, B. Dawant, and J. Fitzpatrick, "Determination of drill paths for percutaneous cochlear access accounting for target positioning error," in Proc. SPIE, vol. 6509, March 2007, p. 650925.1650925.10.
[10] R. Labadie, J. Noble, B. Dawant, R. Balachandran, O. Majdani, and J. Fitzpatrick, "Clinical validation of percutaneous cochlear implant surgery: initial report," Laryngoscope, vol. 118, no. 6, pp. 1031-1039, 2008.
[11] R. Labadie, J. Mitchell, R. Balachandran, and J. Fitzpatrick, "Customized, rapid-production microstereotactic table for surgical targeting: description of concept and in vitro validation," International Journal of Computer Assisted Radiology and Surgery, vol. 4, no. 3, pp. 273-280, 2009.
[12] D. Henderson, "Simple Ceramic Motor. Inspiring Smaller Products," in Actuators 2006, 10th International Conference on New Actuators, vol. 50, June 2006, p. 10.
[13] L. Tsai, Robot analysis: the mechanics of serial and parallel manipulators. Wiley-Interscience, 1999.
[14] R. Balachandran, J. Mitchell, B. Dawant, and J. Fitzpatrick, "Accuracy evaluation of microTargeting Platforms for deep-brain stimulation using virtual targets," IEEE Transactions on Biomedical Engineering, vol. 56, no. 1, pp. 37-44, January 2009.
[15] S. E. Salcudean, P. A. Drexel, D Ben-Dov, A. J. Taylor, and P. D. Lawrence, "A six degree-of-freedom, hydraulic, one person motion simulator," IEEE Intl Conf Rob and Autom, 2437-2443, 1994.
[16] R C Merkle "A new family of six degrees of freedom positional devices" Nanotech. 8 47-52, 1997.
[17] L. Jones, J.-F. Dagenais, W. Danner, and D. Maisonnier, "Design of the Intersector Welding Robot for vacuum vessel assembly and maintenance," Fusion Eng. & Design v 51-52 pp. 979-983, 2000.
[18] M. Shoham, et al., "Robotic assisted spinal surgery" Computer Aided Surgery, 12(2) 105-115, 2007.
[19] F M Warren, R Balachandran, J M Fitzpatrick, R F Labadie, "Percutaneous Cochlear Access Using Bone-Mounted, Customized Drill Guides: Demonstration of Concept In-Vitro," 0 to 1. & Neurotol., 2007, 28(3):325-29.
[20] J. B. West, J. M. Fitzpatrick, S. Toms, C. R. Maurer Jr, and R. J. Maciunas, "Fiducial point placement and the accuracy of point-based, rigid body registration," Neurosurgery v. 48, pp. 810-817, 2001.

What is claimed is:

1. A method of percutaneous cochlear implantation (PCI), comprising the steps of:
   (a) implanting a plurality of anchor members in a skull of a patient surrounding an ear of the patient;
   (b) attaching a prepositioning frame to the plurality of anchor members, the prepositioning frame comprising (i) a prepositioning platform with a central through hole adapted for allowing physical access to the ear during a PCI, and (ii) a plurality of fiducial members protruding from a top surface of the prepositioning platform;
   (c) acquiring a computed-tomography (CT) image of an area of the patient's head including the ear and the plurality of fiducial members;
   (d) determining a centroid of each of the plurality of fiducial members and a trajectory for the PCI according to the CT image;
   (e) configuring a parallel robot by a computer processor according to the CT image, wherein the parallel robot comprises a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform defining a central through hole adapted for allowing the one or more surgical tools to pass therethrough during the PCI, and wherein the computer processor is programmed to set each of the plurality of linear actuators such that the top platform is aligned with the trajectory with respect to the centroids of the plurality of fiducial members to be received by the plurality of receiving mechanisms;
   (f) attaching the parallel robot to the prepositioning frame such that each of the plurality of fiducial members is received by a respective receiving mechanism in the base platform of the parallel robot; and
   (g) performing the PCI using the one or more surgical tools received by the top platform of the parallel robot,
   wherein the prepositioning frame is designed using prior clinical data and the parallel robot is configured according to the CT image such that when the parallel robot is attached to the prepositioning frame, a nominal position of the parallel robot is aligned with an optimal trajectory for the PCI.

2. The method of claim 1, wherein the plurality of anchor members comprises three anchor members.

3. The method of claim 1, wherein the plurality of fiducial members comprises three fiducial members.

4. The method of claim 1, wherein each of the plurality of fiducial members has at least a partial spherical shape.

5. The method of claim 1, wherein each of the plurality of fiducial members is made of titanium.

6. The method of claim 1, wherein the prepositioning platform is made of aluminum or carbon fiber.

7. The method of claim 1, wherein the plurality of linear actuators comprises six linear actuators mounted in pairs to the base platform of the parallel robot and crossing over to three mounting points on the top platform of the parallel robot.

8. The method of claim 1, wherein the parallel robot is adapted for affording six degrees of freedom when the parallel robot is being configured.

9. The method of claim 1, wherein the parallel robot is adapted for affording four degrees of freedom when the parallel robot is being configured.

10. The method of claim 1, wherein the parallel robot is adapted such that the top platform of the parallel robot can be aligned with the trajectory with a precision better than about 0.9 mm.

11. An apparatus for percutaneous cochlear implantation (PCI), comprising:
(a) a prepositioning frame adapted for being attachable to a plurality of anchor members implanted in a skull of a patient surrounding an ear of the patient, the prepositioning frame comprising a prepositioning platform and a plurality of fiducial members protruding from a top surface of the prepositioning platform, the prepositioning platform defining a central through hole adapted for allowing physical access to the ear when the prepositioning frame is attached to the plurality of anchor members for a PCI; and
(b) a parallel robot attached to the prepositioning frame, the parallel robot comprising a top platform and a base platform connected via a plurality of linear actuators, the top platform adapted for receiving one or more surgical tools, the base platform having a plurality of receiving mechanisms, each receiving mechanism adapted for receiving a respective fiducial member of the prepositioning frame, each of the top platform and the base platform defining a central through hole adapted for allowing the one or more surgical tools to pass therethrough during the PCI;
wherein the parallel robot is configurable by a computer processor according to a computed tomography (CT) image acquired when the prepositioning frame is attached to the plurality of anchor members implanted in the skull of the patient, the CT image comprising an image of an area of the patient's head including the ear and the plurality of fiducial members, and wherein the computer processor is programmed to (i) determine a centroid of each of the plurality of fiducial members and a trajectory for the PCI according to the CT image, and (ii) set each of the plurality of linear actuators of the parallel robot such that the top platform of the parallel robot is aligned with the trajectory with respect to the centroids of the plurality of fiducial members; and
wherein the prepositioning frame is designed using prior clinical data and the parallel robot is configured according to the CT image such that when the parallel robot is attached to the prepositioning frame, a nominal position of the parallel robot is aligned with an optimal trajectory for the PCI.

12. The apparatus of claim 11, wherein the plurality of anchor members comprises three anchor members.

13. The apparatus of claim 11, wherein the plurality of fiducial members comprises three fiducial members.

14. The apparatus of claim 11, wherein each of the plurality of fiducial members has at least a partial spherical shape.

15. The apparatus of claim 11, wherein each of the plurality of fiducial members is made of titanium.

16. The apparatus of claim 11, wherein the prepositioning platform is made of aluminum or carbon fiber.

17. The apparatus of claim 11, wherein the plurality of linear actuators comprises six linear actuators mounted in pairs to the base platform of the parallel robot and crossing over to three mounting points on the top platform of the parallel robot.

18. A method of performing an intracranial surgery, comprising the steps of:
(a) implanting three or more anchor members in a skull of a patient;
(b) attaching a prepositioning frame to the three or more anchor members, the prepositioning frame comprising (i) a prepositioning platform with a central through hole adapted for allowing physical access to an area of the patient's brain under surgery, and (ii) three or more fiducial members protruding from a top surface of the prepositioning platform;
(c) acquiring a computed-tomography (CT) image of the area of the patient's brain including the three or more fiducial members;
(d) determining a centroid of each of the three or more fiducial members and a trajectory for the intracranial surgery according to the CT image;
(e) configuring a parallel robot by a computer processor according to the CT image, wherein the parallel robot comprises a top platform and a base platform connected via a plurality of linear actuators, the top platform adapted for receiving one or more surgical tools, the base platform having a plurality of receiving mechanisms, each receiving mechanism adapted for receiving a respective fiducial member, each of the top platform and the base platform defining a central through hole adapted for allowing the one or more surgical tools to pass therethrough during the intracranial surgery, and wherein the computer processor is programmed to set each of the plurality of linear actuators such that the top platform is aligned with the trajectory with respect to the centroids of the three or more fiducial members to be received by the plurality of receiving mechanisms;
(f) attaching the parallel robot to the prepositioning frame such that each of the three or more fiducial members is received by a respective receiving mechanism in the base platform of the parallel robot; and
(g) performing the intracranial surgery using the one or more surgical tools received by the top platform of the parallel robot,
wherein the prepositioning frame is designed using prior clinical data and the parallel robot is configured according to the CT image such that when the parallel robot is attached to the prepositioning frame, a nominal position of the parallel robot is aligned with an optimal trajectory for the intracranial surgery.

19. The method of claim 18, wherein each of the three or more fiducial members has at least a partial spherical shape.

20. The method of claim 18, wherein each of the three or more fiducial members is made of titanium.

21. The method of claim 18, wherein the prepositioning platform is made of aluminum or carbon fiber.

22. The method of claim 18, wherein the plurality of linear actuators comprises six linear actuators mounted in pairs to the base platform of the parallel robot and crossing over to three mounting points on the top platform of the parallel robot.

* * * * *